United States Patent
Niederauer et al.

(10) Patent No.: US 10,105,265 B2
(45) Date of Patent: Oct. 23, 2018

(54) DRESSING FOR WOUND TREATMENT

(71) Applicant: ELECTROCHEMICAL OXYGEN CONCEPTS, INC., San Antonio, TX (US)

(72) Inventors: Mark Q. Niederauer, San Antonio, TX (US); James P. Daley, San Antonio, TX (US); Alan S. Neil, Indian Shores, FL (US)

(73) Assignee: ELECTROCHEMICAL OXYGEN CONCEPTS, INC., San Antonio, TX (US)

( * ) Notice: Subject to any disclaimer, the term of this patent is extended or adjusted under 35 U.S.C. 154(b) by 455 days.

(21) Appl. No.: 14/767,046

(22) PCT Filed: Feb. 11, 2014

(86) PCT No.: PCT/US2014/015715
§ 371 (c)(1),
(2) Date: Aug. 11, 2015

(87) PCT Pub. No.: WO2014/126888
PCT Pub. Date: Aug. 21, 2014

(65) Prior Publication Data
US 2016/0000611 A1 Jan. 7, 2016

Related U.S. Application Data

(60) Provisional application No. 61/763,872, filed on Feb. 12, 2013.

(51) Int. Cl.
*A61F 13/00* (2006.01)
*A61F 13/02* (2006.01)

(52) U.S. Cl.
CPC .... *A61F 13/0216* (2013.01); *A61F 13/00068* (2013.01); *A61F 13/022* (2013.01);
(Continued)

(58) Field of Classification Search
CPC ............ A61F 13/0216; A61F 13/00068; A61F 13/0213; A61F 13/022; A61F 13/0226;
(Continued)

(56) References Cited

U.S. PATENT DOCUMENTS 4,969,881 A 11/1990 Viesturs
6,458,109 B1 10/2002 Henley
(Continued)

FOREIGN PATENT DOCUMENTS

CN 101917947 1/2011
JP S62-231676 10/1987
(Continued)

OTHER PUBLICATIONS

English Translation of JP S62-231676, received on Nov. 27, 2017.
(Continued)

*Primary Examiner* — Ophelia A Hawthorne
(74) *Attorney, Agent, or Firm* — Parker Highlander PLLC

(57) ABSTRACT

Examples include devices, systems and methods related to advanced wound therapy dressings. Specific examples are optimized for use with mobile continuous diffusion of oxygen therapy systems for the localized delivery of oxygen to damaged and healing tissues. Examples may utilize a conduit to deliver therapeutic fluids, including for example oxygen, where the conduit comprises a plurality of apertures or perforations. Examples may also include a spacer material with a plurality of distribution channels in fluid communication with the conduit.

38 Claims, 12 Drawing Sheets

(52) U.S. Cl.
CPC ........ *A61F 13/025* (2013.01); *A61F 13/0213* (2013.01); *A61F 13/0226* (2013.01); *A61F 13/0253* (2013.01); *A61F 2013/0017* (2013.01); *A61F 2013/00604* (2013.01); *A61F 2013/00731* (2013.01)

(58) Field of Classification Search
CPC ................ A61F 13/025; A61F 13/0253; A61F 2013/0017; A61F 2013/00604; A61F 2013/00731; A61F 13/00; A61F 13/02; A61F 2013/00536; A61F 2013/00217; A61F 2013/0054
See application file for complete search history.

(56) References Cited

U.S. PATENT DOCUMENTS

| | | | |
|---|---|---|---|
| 7,216,651 | B2 | 5/2007 | Argenta |
| 7,263,814 | B2 | 9/2007 | Rosati |
| 7,429,252 | B2 | 9/2008 | Sarangapani |
| 7,790,945 | B1 | 9/2010 | Waston |
| 7,938,790 | B2 | 5/2011 | Fleischmann |
| 8,084,663 | B2 | 12/2011 | Watson |
| 8,088,113 | B2 | 1/2012 | Scherson et al. |
| 8,235,955 | B2 * | 8/2012 | Blott .................. A61M 1/0037 604/305 |
| 8,287,506 | B2 | 10/2012 | Wells |
| 2001/0041188 | A1 | 11/2001 | Gibbins |
| 2003/0212357 | A1 * | 11/2003 | Pace .................. A61F 13/0203 602/41 |
| 2006/0041238 | A1 | 2/2006 | Bowen |
| 2006/0282028 | A1 | 12/2006 | Howard et al. |
| 2007/0027414 | A1 * | 2/2007 | Hoffman ............ A61M 1/0088 602/2 |
| 2007/0185426 | A1 * | 8/2007 | Ambrosio ................ A61L 27/52 602/43 |
| 2008/0058735 | A1 | 3/2008 | Rosati et al. |
| 2009/0216204 | A1 | 8/2009 | Bhavaraju et al. |
| 2009/0227969 | A1 | 9/2009 | Jaeb et al. |
| 2010/0204663 | A1 * | 8/2010 | Wudyka ............ A61M 1/0088 604/313 |
| 2010/0222654 | A1 * | 9/2010 | Gonopolskiy ....... A61B 5/0059 600/310 |
| 2010/0262092 | A1 * | 10/2010 | Hartwell ............ A61F 13/023 604/304 |
| 2010/0305490 | A1 * | 12/2010 | Coulthard ........... A61M 1/0088 602/43 |
| 2011/0130712 | A1 | 6/2011 | Topaz |
| 2011/0224631 | A1 | 9/2011 | Simmons et al. |
| 2012/0016322 | A1 * | 1/2012 | Coulthard ........... A61M 1/0031 604/319 |
| 2012/0046603 | A1 | 2/2012 | Vinton |
| 2012/0330253 | A1 | 12/2012 | Robinson et al. |

FOREIGN PATENT DOCUMENTS

| | | |
|---|---|---|
| JP | 2008-539966 | 11/2008 |
| JP | 2011-505887 | 3/2011 |
| JP | 2011-514209 | 5/2011 |
| WO | WO 2002/043634 | 6/2002 |
| WO | WO 2005/094744 | 10/2005 |
| WO | WO 2006/114637 | 11/2006 |
| WO | WO 2006/122169 | 11/2006 |
| WO | WO 2009/066104 | 5/2009 |
| WO | WO 2009/071932 | 6/2009 |
| WO | WO 2009/111655 | 9/2009 |
| WO | WO 2010/008167 | 1/2010 |
| WO | WO 2010/139926 | 12/2010 |
| WO | WO 2011/112774 | 9/2011 |

OTHER PUBLICATIONS

Hunt and Pai, "The effect of varying ambient oxygen tensions on wound metabolism and collagen synthesis", *Surg Gynecol Obstet* 135:561-567, 1972.
Office Communication issued in Japanese Application No. 2015-557192, dated Nov. 13, 2017. (English Translation).
Bosco et al., "The hypoxic synovial environment regulates expression of vascular endothelial growth factor and osteopontin in juvenile idiopathic arthritis", *J Rheumatol* 36:1318-1329, 2009.
Extended European Search Report issued in European Application No. 14751642.1, dated Sep. 15, 2016.
Hohn et al., "Effect of O2 tension on microbicidal function of leukocytes in wounds and in vitro", *Surg Forum* 27:18-20, 1976.
International Preliminary Report on Patentability issued in International Application No. PCT/US2014/015715, dated Aug. 18, 2015.
International Search Report and Written Opinion issued in International Application No. PCT/US2014/015715, dated Nov. 20, 2014.
Knighton et al., "Regulation of wound-healing angiogenesis-effect of oxygen gradients and inspired oxygen concentration", *Surgery* 90:262-270, 1981.

* cited by examiner

DRESSING FOR WOUND TREATMENT

CROSS-REFERENCE TO RELATED APPLICATIONS

This application is a national phase application under 35 U.S.C. § 371 of International Application No. PCT/US2014/015715, filed Feb. 11, 2014, which claims priority to U.S. Provisional Patent Application Ser. No. 61/763,872, filed Feb. 12, 2013, the contents of each of which are incorporated by reference herein.

BACKGROUND INFORMATION

I. Field of the Invention

Embodiments of the present invention relate generally to the field of advanced wound therapy involving the use of localized therapeutic fluid delivery to damaged and healing tissues and in specific embodiments, dressings optimized for use with mobile continuous diffusion of oxygen therapy systems.

II. Background and Description of Related Art

Damaged tissue, including skin and soft tissue wounds, triggers an increase in demand for oxygen. Oxygen has been reported to increase fibroblast migration and replication (Knighton, et al.), increase the rate of collagen production and tensile strength of collagen fibers (Hunt, et al.), stimulate angiogenesis (Knighton, et al.), promote macrophage chemotaxis (Bosco, et al.), and enhance the antibacterial activities of leukocytes, including phagocytic function (Hohn et al.), thereby increasing the removal of cell debris and promoting physiological wound debrisment.

There are two ways in which damaged moist tissues can get oxygen: (1) it can be absorbed through the lungs and carried through the cardiovascular/respiratory system to the wound site; or (2) oxygen may be supplied to the wound directly, either by contact with oxygen in ambient air (at a concentration of about 21%) or by pure oxygen (100%), delivered by an external oxygen source and administration apparatus designed for this purpose. In both cases, oxygen reaches the cells of such damaged tissue by diffusion, which is relevant for the skin and soft tissue wounds to which embodiments of the present disclosure are directed.

In many patients, for example patients with venous stasis ulcers, diabetic foot ulcers, some pressure ulcers and other wounds, normal delivery of oxygen via the cardiovascular/respiratory system is compromised. While there may be sufficient blood supply to a local area to maintain normal physiological processes, including the maintenance of dermal and epidermal tissues, the oxygen capable of being supplied to a local area in patients with compromised vascularity is often insufficient to supply oxygen at the greater amounts needed to fuel cellular processes for repair of damaged tissues, even when advanced wound care modalities such as vacuum-assisted closure techniques are used. The occlusive dressings used with this and some other wound closure methodologies can restrict access of these hypoxic tissues to oxygen which may otherwise diffuse into a moist wound from the ambient air, decreasing the likelihood of wound closure in those clinical situations in which adequate flow to and from the tissues cannot be restored.

Advanced wound care treatments such as Topical Oxygen Therapy (TOT), also known as Topical Hyperbaric Oxygen Therapy (THOT), deliver pure oxygen to wounds, but because these systems are not portable, and their use immobilizes the patient. Treatment time with these systems is therefore typically limited to about 90 minutes per day. As the cells in a healing wound have continuous need for oxygen, the limited duration of therapy practically possible with these modalities may limit their clinical utility.

SUMMARY

In patients with wounds in whom normal delivery of oxygen via the cardiovascular/respiratory system is compromised, one goal of oxygen therapy is to provide an uninterrupted and continuous supply of externally-supplied oxygen to a moist wound. It is desirable that the oxygen be supplied in a manner that most closely approximates the normal diffusion of oxygen in normal tissues but at a rate sufficient to fuel the increased oxygen demands required in healing tissues. This therapy is known as Continuous Diffusion of Oxygen therapy.

The TransCu $O_2$® device, available from $EO_2$ Concepts, is a non-invasive, electrochemical low-dose tissue oxygenation system intended to be used for the treatment of chronic wounds such as diabetic foot ulcers, venous leg ulcers, pressure ulcers and other skin wounds through the continuous diffusion of oxygen. The TransCu $O_2$® device is one of several devices in a class known to supply Continuous Diffusion of Oxygen (CDO) therapy. To achieve maximum therapeutic benefit with this class of devices, it is important to maximize the area of an oxygen-compromised wound that receives a continuous and balanced supply of pure oxygen, while simultaneously maintaining a moist wound healing environment, and allowing patients to remain ambulatory.

The TransCu $O_2$® device was originally intended to be used with available lower-cost wound dressings and/or whichever dressings the treating clinician chose to use capable of maintaining a moist wound environment. While this practice is advantageous in that it is consistent with the standard treatment protocols at a given facility, this practice may contribute to inter-institutional differences in clinical outcomes.

As flowing oxygen will take the path of least resistance, areas of a wound dressing that have become saturated with wound exudate may not receive the concentration of oxygen that areas not saturated with wound exudate (but that overlay an otherwise normal moist wound) would receive. In addition, imbalanced and/or inconsistent oxygen flow may lead to wounds with inconsistent and "patchy" levels of oxygen diffusion into the wound surface. The potential also exists for the distal end of the oxygen delivery cannula placed in the dressed wound to become clogged with fluids and/or tissue from the wound, which could result in the interruption in an otherwise continuous flow of therapeutic oxygen.

Specific exemplary embodiments of the present disclosure comprise a dressing that can allow for a more consistent and balanced flow of oxygen to substantially all parts of a dressed wound, including those with exudate saturation overlying a particular part of a dressed wound.

Exemplary embodiments of the present disclosure comprise a dressing for wound treatment comprising: an occlusive layer; a spacer material; a plurality of distribution channels; a first layer, where the spacer material is located between the occlusive layer and the first layer; and a first conduit in fluid communication with the plurality of distribution channels.

In particular embodiments, the distribution channels can be formed in the spacer material. In certain embodiments, the plurality of distribution channels can comprise additional conduits in fluid communication with the first conduit, and where the additional conduits are adjacent to the spacer material. Particular embodiments can further comprise a second absorbent layer located between the spacer material and the occlusive layer.

In certain embodiments, the second absorbent layer can comprise an alginate, and in some embodiments the occlusive layer can comprise an adhesive. In specific embodiments, the occlusive layer can comprise a first surface proximal to the spacer material, a second surface distal to the spacer material, and a perimeter extending around the occlusive layer, where the adhesive extends around the perimeter of the first surface. In some embodiments, the adhesive can comprise a hydrocolloid.

In particular embodiments, the first layer can comprise a first surface proximal to the spacer material and a second surface distal to the spacer material, and the second surface can be a non-adherent surface. Certain embodiments can further comprise a non-adherent layer, where the first layer is located between the non-adherent layer and the spacer material. In specific embodiments the first layer can be an absorbent layer, while in some embodiments the first layer can be a contact layer. In particular embodiments the first layer can be configured as a silicone non-adherent layer.

In some embodiments the first conduit comprises a first end proximal to spacer material and a second end distal to the spacer material, and in specific embodiments the first conduit comprises a plurality of apertures. In certain embodiments the plurality of apertures can be proximal to the first end of the first conduit. In specific embodiments the plurality of apertures can be arranged along an axial length of the first conduit. In specific embodiments the plurality of apertures can be arranged in order of increasing diameter toward the first end of the first conduit.

In certain embodiments a first aperture can be proximal to the first end and a second aperture can be distal to the first end, and the diameter of the first aperture is greater than or equal to the diameter of a second aperture. In particular embodiments the distance between the first aperture and the first end of the first conduit is less than the distance between the first end of the first conduit and the second aperture; and the diameter of the first aperture is greater than or equal to the diameter of the second aperture. Certain embodiments may comprise a third aperture, where: the distance between the third aperture and the first end of the first conduit is greater than the distance between the second aperture and the first end of the first conduit; and the diameter of the second aperture is greater than or equal to the diameter of the third aperture.

In particular embodiments, the first conduit comprises a first aperture, a second aperture, and a third aperture, where: the first aperture is located a first distance from the first end of the first conduit; the second aperture is located a second distance from the first end of the first conduit; the third aperture is located a third distance from the first end of the first conduit; the first distance is less than the second distance; the second distance is less than the third distance; the diameter of the first aperture is greater than or equal to the diameter of the second aperture; and the diameter of the second aperture is greater than or equal to the diameter of the third aperture.

Certain embodiments can further comprise a plurality of conduits in fluid communication with the plurality of distribution channels. In certain embodiments the first conduit can comprise a first lumen and a second lumen. In specific embodiments, during use a first fluid flows through the first lumen and a second fluid flows through the second lumen. In particular embodiments, during use a positive pressure is applied to the first lumen and a negative pressure is applied to the second lumen. In some embodiments, the first conduit can be configured to withstand a compressive pressure of 200 mm Hg without occluding a fluid flow through the conduit.

Certain embodiments can further comprise can oxygen delivery device coupled to the first conduit. Particular embodiments can further comprise a source of fluid flow coupled to the first conduit. In specific embodiments the source of fluid flow can be configured to provide a variable flow rate of a fluid, and in particular embodiments the source of fluid flow can be configured to alter a fluid flow rate based on an output from a sensor. In certain embodiments, the sensor can be configured to measure temperature, pH or other variables.

In particular embodiments the plurality of distribution channels can comprise channels that extend from a central region of the spacer material toward a perimeter of the spacer material. In specific embodiments, the plurality of distribution channels can comprise eight channels that extend from a central region of the spacer material toward a perimeter of the spacer material. In some embodiments, the plurality of distribution channels can be configured in a spiral or concentric pattern.

In particular embodiments the spacer material has a length and a width; each of the distribution channels has a length; the combined length of the distribution channels is greater than the length of the spacer material; and the combined length of the distribution channels is greater than the width of the spacer material. In specific embodiments, at least one of the plurality of distribution channels is at least 25 mm long. In particular embodiments, at least one of the plurality of distribution channels is at least 5 mm wide.

Certain embodiments comprise a dressing for wound treatment comprising: an occlusive layer; a spacer material; a first layer, where the spacer material is located between the occlusive layer and the first layer; and a first conduit in fluid communication with the spacer material, where the conduit comprises a plurality of apertures. Particular embodiments can further comprise a plurality of distribution channels.

In particular embodiments, the spacer material has a length, a width, and a thickness, and at least one of the distribution channels has a length that is at least twenty percent of the length of the spacer material. In specific embodiments, at least one of the distribution channels has a length that is at least twenty percent of the width of the spacer material. In certain embodiments at least one of the distribution channels has a length that is at least five hundred percent of the thickness of the spacer material. In particular embodiments the plurality of apertures comprise a first aperture with a first diameter and a second aperture with a second diameter, and wherein the first diameter is larger than or equal to the second diameter.

Certain embodiments can also comprise a method of providing a therapeutic fluid to a wound using a dressing for wound treatment. In specific embodiments, the dressing for wound treatment can comprise: an occlusive layer; a spacer material; a plurality of distribution channels; a first layer, where the spacer material is located between the occlusive layer and the first layer; and a first conduit in fluid communication with the plurality of distribution channels. In particular embodiments, the method of providing therapeutic fluid to a wound comprises: providing the dressing for wound treatment; placing the first layer in contact with the wound; and delivering a therapeutic fluid through the first conduit to the plurality of distribution channels.

Exemplary embodiments can also comprise a method of providing a therapeutic fluid to a wound using a dressing for wound treatment, where the dressing comprises: an occlusive layer; a spacer material; a first layer, wherein the spacer material is located between the occlusive layer and the first layer; and a conduit comprising a plurality of apertures. In particular embodiments, the method can comprise providing the dressing for wound treatment; placing the first layer in contact with the wound; and delivering a therapeutic fluid through the conduit to the spacer material, wherein the conduit comprises a plurality of apertures.

In certain embodiments the methods can further comprise: measuring a first parameter; and adjusting a second parameter related to the delivery of the therapeutic fluid through the first conduit.

In certain embodiments, the first parameter can be a temperature reading, a pressure reading, or a pH reading, and the second parameter can be a flow rate or a pressure. In particular embodiments, the therapeutic fluid can be pure oxygen.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or." The use of the term "fluid" includes both liquid and gasses.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of this disclosure, are given by way of illustration only, since various changes and modifications within the spirit and scope of the invention will be apparent to those skilled in the art from this detailed description.

DETAILED DESCRIPTION OF ILLUSTRATIVE EMBODIMENTS

Figure 1:
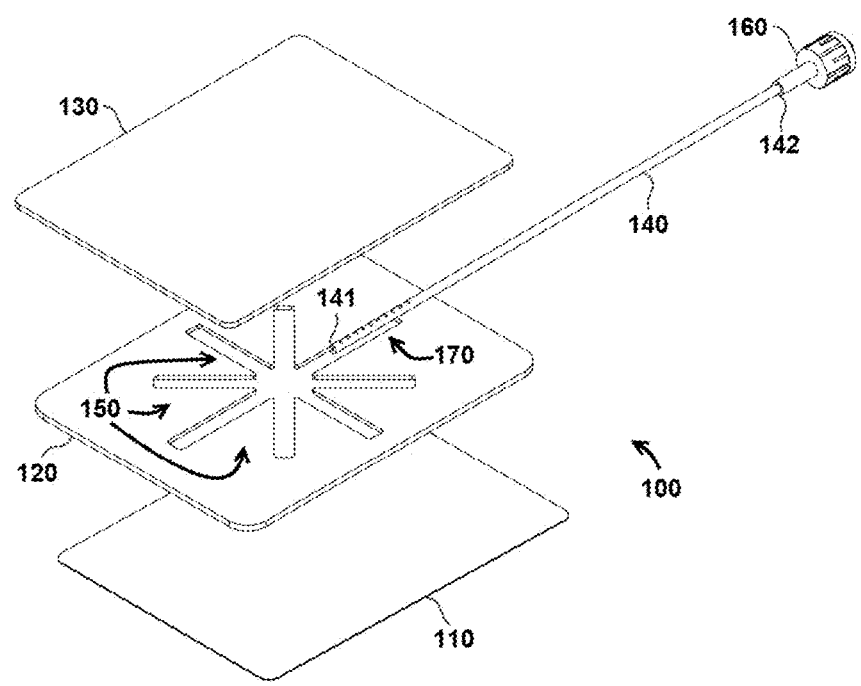
FIG. 1 is an exploded perspective view of a wound dressing according to an embodiment of the present disclosure.
Figure 2:
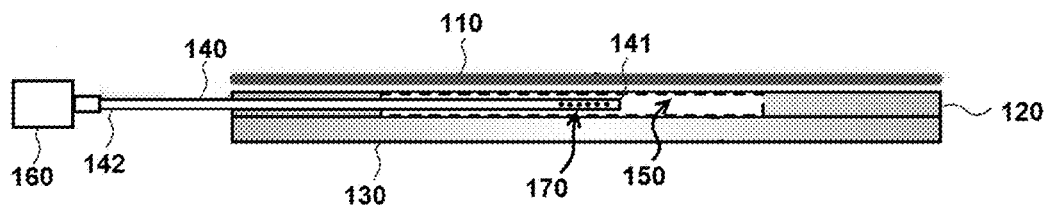
FIG. 2 is a section view of the embodiment of FIG. 1.

Referring now to FIGS. 1-2, a first exemplary embodiment of a dressing 100 for wound treatment comprises an occlusive layer 110, a spacer material 120, a first layer 130 and a conduit 140. In this embodiment, spacer material 120 is located between occlusive layer 110 and first layer 130, and spacer material 120 comprises a plurality of distribution channels 150 in fluid communication with conduit 140.

In the embodiment shown, conduit 140 also comprises a first end 141 proximal to spacer material 120 and distribution channels 150. Conduit 140 also comprises a second end 142 distal to spacer material 120 and distribution channels 150. In this illustrated embodiment, conduit 140 comprises a plurality of apertures 170 proximal to a first end 141 of conduit. It is understood that in other embodiments, conduit 140 may comprise a single aperture. Conduit 140 also comprises a coupling mechanism 160 proximal to second end 142 of conduit 140. In particular embodiments, coupling mechanism 160 may be configured to couple to a source of fluid flowing to dressing 100, and in certain embodiments coupling mechanism 160 may be configured to couple to a source of oxygen flow provided to dressing 100. In specific embodiments, coupling mechanism 160 may be a Luer lock device configured to couple to a TransCu O$_2$® device available from EO$_2$ Concepts Inc., located in San Antonio, Tex.

Figure 3:
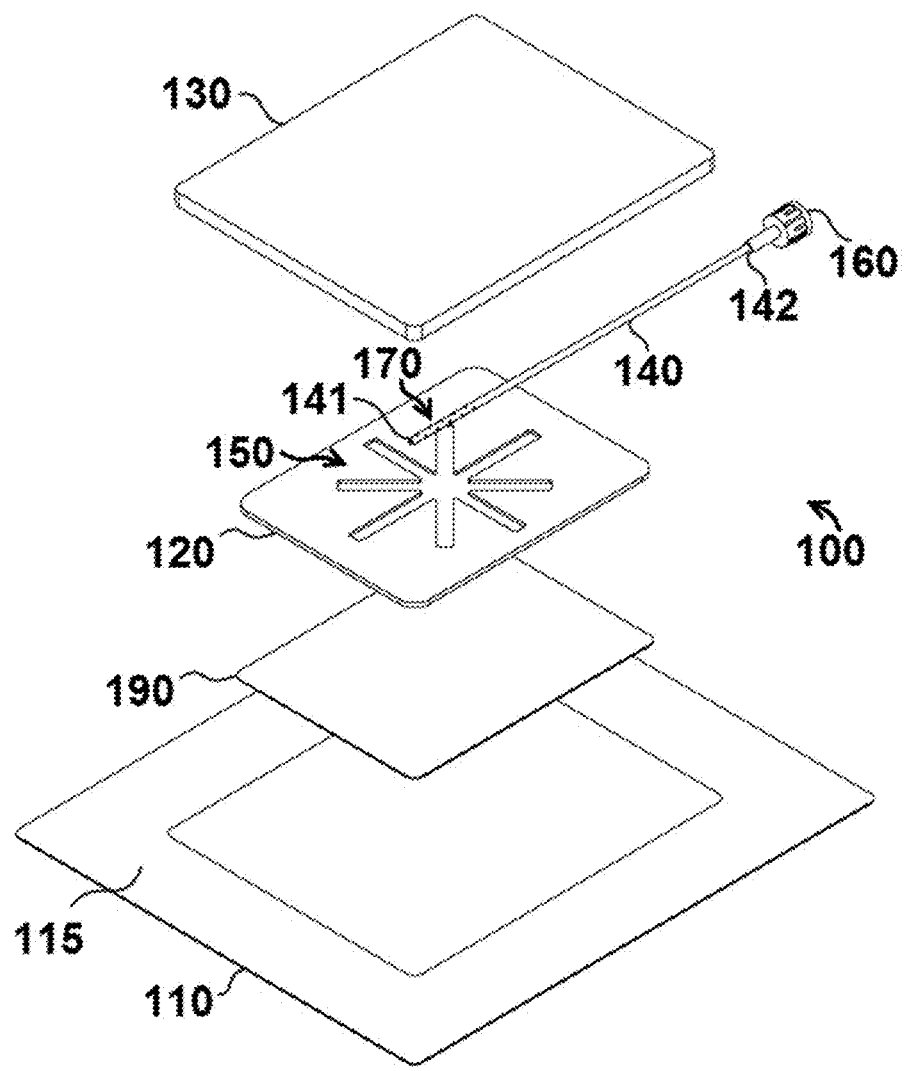
FIG. 3 is an exploded perspective view of the embodiment of FIG. 1 with additional components.

Referring now to FIG. 3, dressing 100 may also comprise a second absorbent layer 190 between occlusive layer 110 and spacer material 120. In addition, in the embodiment shown in FIG. 3, occlusive layer 110 may also comprise an adhesive 115 that extends around the perimeter of the surface of occlusive layer 110. During use, adhesive 115 can be used to adhere to a patient's skin around a wound and seal or isolate the wound area from the outside environment. Dressing 100 may be used to treat various types of wounds, including for example, skin ulcerations due to diabetes, venous stasis, post surgical infections, gangrenous lesions, pressure ulcers, infected residual limbs, skin grafts, burns, and frostbite.

As described in more detail below, conduit 140 may be a kink-resistant simple tube, tubing with apertures or perforations, a porous tubing, branched tubing, multiple tubes, a single conduit with one or more separate lumens or any other configuration that allows for the flow of fluids to or from the distribution channels 150. In certain exemplary embodiments, apertures 170 in conduit 140 may be the same size or vary in size depending on the application (e.g., the holes may become progressively larger as they approach first end 141 of conduit 140 that is positioned proximal to spacer material 120).

In certain embodiments, conduit 140 may be a generally flat, flexible oxygen-permeable tape or membrane section that is attached as to a distal end of a cylindrical tube and that delivers therapeutic fluid along the entire surface of the tape or membrane. Conduit 140 can be coupled to a source of therapeutic fluid (and/or in some embodiments, a vacuum, through coupling mechanism 160). Conduit 140 may have multiple branches or junctions that allow different portions of conduit 140 to terminate at different points in (or adjacent) spacer material 120 so that a therapeutic fluid (e.g. oxygen) may be directly delivered to multiple points within dressing 100. In some situations, multiple conduits or multiple lumens in a single conduit may be provided in dressing 100 to perform different functions including, for example, therapeutic material delivery, fluid removal, etc.

Occlusive layer 110 may be a film or other material that is occlusive or semi-occlusive to provide a non-permeable or semi-permeable layer that assists in keeping oxygen or other therapeutic fluids delivered through conduit 140 adjacent the wound site.

In exemplary embodiments, first layer 130 and the spacer material 120 may be made from any foam, alginate, or other dressing material that can draw fluids away from the wound site and allow for the delivery of therapeutic fluids to the wound site. In certain embodiments, first layer 130 may be configured as an absorbent layer to retain liquid (e.g. via a fluid-retaining polymer). In other embodiments, first layer 130 may be configured as a separation or contact layer with minimal liquid retention properties, such as a silicone non-adherent layer.

In particular embodiments, spacer material 120 can be configured as an open-cell foam. Spacer material 120 is located between first layer 130 and occlusive layer 110 (as well as second absorbent layer 190 in certain embodiments) to provide a flow path for a therapeutic fluid to be delivered through conduit 140 to a wound site. During use, second absorbent layer 190 can function to keep distribution channels 150 in spacer material 120 open under a wider range of exudate levels. In specific embodiments, dressing 100 can be configured to provide a flow of between 1-200 ml/hr of oxygen at an average pressure between 1.0 to 1.0263 atm absolute.

In specific embodiments, dressing 100 can be configured to function adequately at a pressures ranging from about −200 mm Hg to about 200 mm Hg.

In addition to or in place of the layers described above, hydrocolloids, composites, hydrogels, collagens, contact layers, alignates, silver elements, antibiotics or antimicrobials, pharmaceutical therapies, biologics, biosynthetics, enzymatic debriding agents, wound fillers, transparent or thin films, gauze, and/or other wound therapy modalities may be incorporated into dressing 100.

Many modifications and variations can be provided to dressing 100. For example, dressing 100 may be provided with an integrated conduit 140, or conduit 140 may be separate and then inserted in spacer material 120 before applying dressing 100 to a wound site. In embodiments where occlusive layer 110 does not comprise adhesive 115, dressing 100 may be secured to the patient via thin film, gauze, an elastic bandage or other mechanisms.

During operation, dressing 100 can be used to provide therapeutic fluid to a wound site. In specific embodiments, dressing 100 can be used to provide an oxygen-enriched micro-environment around a wound site to optimize the healing process. In certain exemplary embodiments in operation on a wound site, dressing 100 includes first layer 130 engaging the wound, spacer material 120 adjacent first layer 130, conduit 140 adjacent spacer material 120 such that it may supply a therapeutic fluid (e.g. oxygen) to distribution channels 150 in spacer material 120. During operation, first layer 130 can provide a barrier between a therapeutic fluid (e.g. infused oxygen) and the wound.

Dressing 100 may also comprise second absorbent layer 190 adjacent spacer material 120, and occlusive layer 110 adjacent second absorbent layer 190 with adhesive 115 that engages the skin around the wound site to provide a seal. Such a configuration can create an oxygen enriched micro-environment when conduit 140 is providing oxygen, e.g. via an oxygen diffusion device coupled to coupling mechanism 160.

In exemplary embodiments of the present disclosure, apertures 170 and distribution channels 150 in spacer material 120 can be configured to provide the distribution of oxygen throughout dressing 100 across the surface of the wound site in a manner that is more uniform than prior systems. Prior systems that provide a single point of oxygen delivery and/or a dressing without distribution channels can create an uneven distribution of oxygen across the wound surface. In such systems, the oxygen delivered will move toward the area of lowest pressure (e.g. "follow the path of least resistance") and therefore will not necessarily reach areas of the wound that are remote from the delivery point or points (e.g., the locations at which the fluid exits conduit 140 and/or engages the spacer material 120).

While the spacer material and absorbent layers of prior art dressings may be configured to allow fluid flow, the pressure drop across such dressings can create uneven distribution of thereapeutic fluids. Such pressure drops can be exacerbated when the dressing materials contain liquid (including for example, wound exudate) and the therapeutic fluid is a gas being delivered at relatively low pressures. This can be a particular issue in oxygen enrichment therapy, where it is desirable to maintain a moist wound surface.

Other factors may also lead to unequal distribution of therapeutic fluid. For example, certain patients may be sensitive or allergic to adhesives, which can prevent the dressing from being sealed around the wound site. This can leave the perimeter edges of the dressing materials exposed to atmospheric pressure and promote the migration of therapeutic fluid from the delivery point to the closest perimeter edge, resulting in uneven distribution of the therapeutic fluid.

Embodiments of the present disclosure provide for multiple delivery points by providing multiple apertures and/or distribution channels in the spacer material or adjacent the spacer material. Minimizing the distance from a fluid delivery point to the furthest region of a wound can decrease the diffusion distance across the dressing and increase the amount of therapeutic fluid that reaches that wound region. Decreasing the diffusion distance increases not only the concentration of the therapeutic fluid that reaches the wound region, it also increases the rate at which the therapeutic fluid is delivered to the wound region. This can provide for faster wound healing times and improved patient outcomes.

The implementation of multiple apertures 170 in conduit 140 and/or distribution channels 150 in spacer material 120 also reduces the likelihood that thereapeutic fluid flow will be significantly restricted or stopped during use. For example, blockage of fluid flow can be a particular concern as wound exudate enters a wound dressing. With multiple pathways for therapeutic fluid to enter wound dressing, it is less likely that a blockage will restrict the flow of therapeutic fluid.

Figure 4:
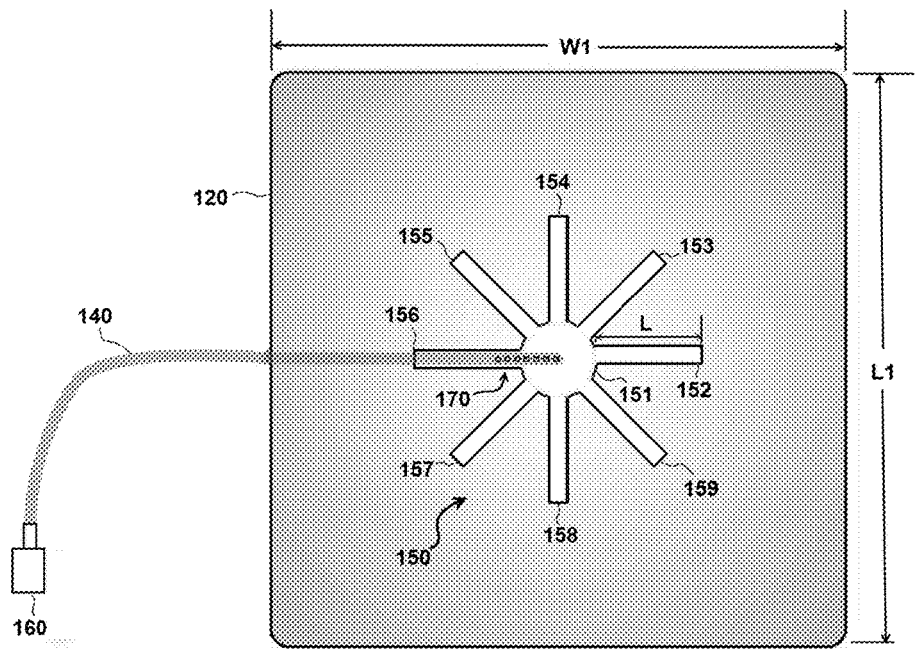
FIG. 4 is a top view of the spacer material and conduit of the embodiment of FIG. 1.

Referring now to FIG. 4, the illustrated pattern of distribution channels 150 can allow therapeutic fluid to exit apertures 170 into a central region 151 of distribution channels 150 and then migrate (with minimal pressure drop) outwardly from central region 151 into individual channels 152-159. The interface of spacer material 120 with individual channels 152-159 and central region 151 provides for an increased surface area and multiple avenues for therapeutic fluid to be distributed throughout spacer material 120. The pressure throughout spacer material 120 will also be more uniform because the pressure drop of the fluid traveling through distribution channels 150 is less than the pressure drop the fluid would experience if it had to travel entirely through spacer material 120 to reach the perimeter regions of spacer 120.

In exemplary embodiments, the distribution channels 150 in spacer material 120 may be created by removing material from spacer material 120, inserting porous tubes into spacer material 120, and/or through any other method for creating channels for the distribution or extraction of fluids. In specific embodiments, distribution channels 150 may be formed by stamping a pattern or cutting material from spacer material 120.

Conduit 140 may also be used provide a vacuum to draw fluids away from the wound site. As such, the distribution channels 150 (and conduit 140) in spacer material 120 are configured to both deliver and/or extract fluids, including nebulized liquids, antibiotics, pharmaceutical therapies, biologics, and/or other therapeutic materials to and from the wound site. In certain embodiments, conduit 140 may be configured as a multi-lumen conduit that delivers fluid to dressing 100 via a first lumen and draws fluid from dressing 100 via a second lumen.

FIG. 4 illustrates a top view of spacer material 120 and conduit 140. In the embodiment shown in FIG. 4, distribution channels 150 comprise eight individual channels 152-159 that extend from central region 151 of spacer material 120 toward a perimeter of the spacer material. It is understood that in other embodiments, there may be a different number of individual channels, or channels arranged in other patterns, including, for example, a concentric pattern.

In one specific embodiment, spacer material 120 may have a length L1 of approximately 100 mm and a width W1 of approximately 80 mm. In a specific embodiment, each distribution channel 152-159 may have a length L of approximately 25 mm and a width W of approximately 5 mm. In certain embodiments, the combined length L of each distribution channel is greater than the length L1 or the width W1 of the spacer material (e.g. 8×25 mm=200 mm, which is greater than 100 mm or 80 mm). It is understood that the dimensions provided above are merely exemplary of one embodiment, and that other embodiments may comprise different dimensions. The use of multiple channels 150 within or adjacent to spacer material 120 can provide for a lower pressure drop across spacer material 120 than other configurations, including, for example, a single channel extending across spacer material 120.

Figure 5:
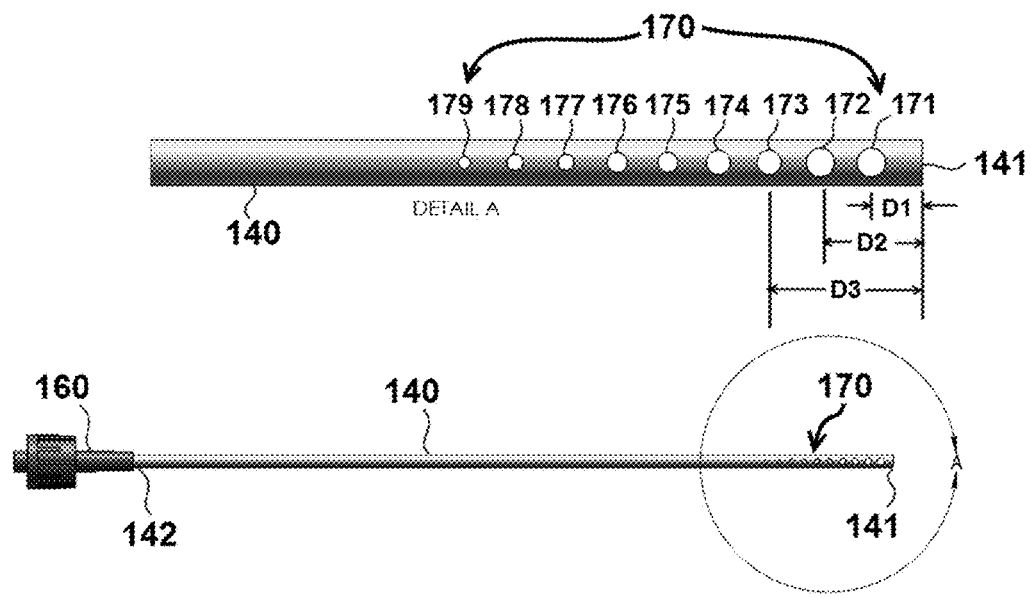
FIG. 5 is a top view and a detail view of the conduit of the embodiment of FIG. 1.

As shown in FIG. 5, apertures 170 of conduit 140 may be arranged in order of increasing diameter toward first end 141 of conduit 140. For example, a first aperture 171 proximal to first end 141 has a diameter that is greater than or equal to the diameter of a second aperture 172 that is proximal to first end 141. More specifically, a distance D1 between first aperture 171 and first end 141 is less than a distance D2 between first end 141 and second aperture 172. In the embodiment shown, a distance D3 between a third aperture 173 and first end 141 is also greater than distance D2, and the diameter of aperture 172 is greater than or equal to the diameter of aperture 173. The remaining apertures 174-179 are also of generally decreasing diameter as the distance from the apertures to first end 141 increases. The variation in aperture diameters can equalize the amount of fluid flow that exits each aperture due to the pressure drop as the fluid travels through the conduit. During use, the larger apertures will be subjected to a lower pressure. Therefore, increasing the size of the aperture can allow the fluid exiting the apertures at lower pressure regions to be more consistent with fluid flow rates from apertures in higher pressure regions. It is understood that other embodiments may have different arrangements of apertures, including apertures spaced around the circumference of conduit 140, including for example, a spiral pattern.

Figure 6:
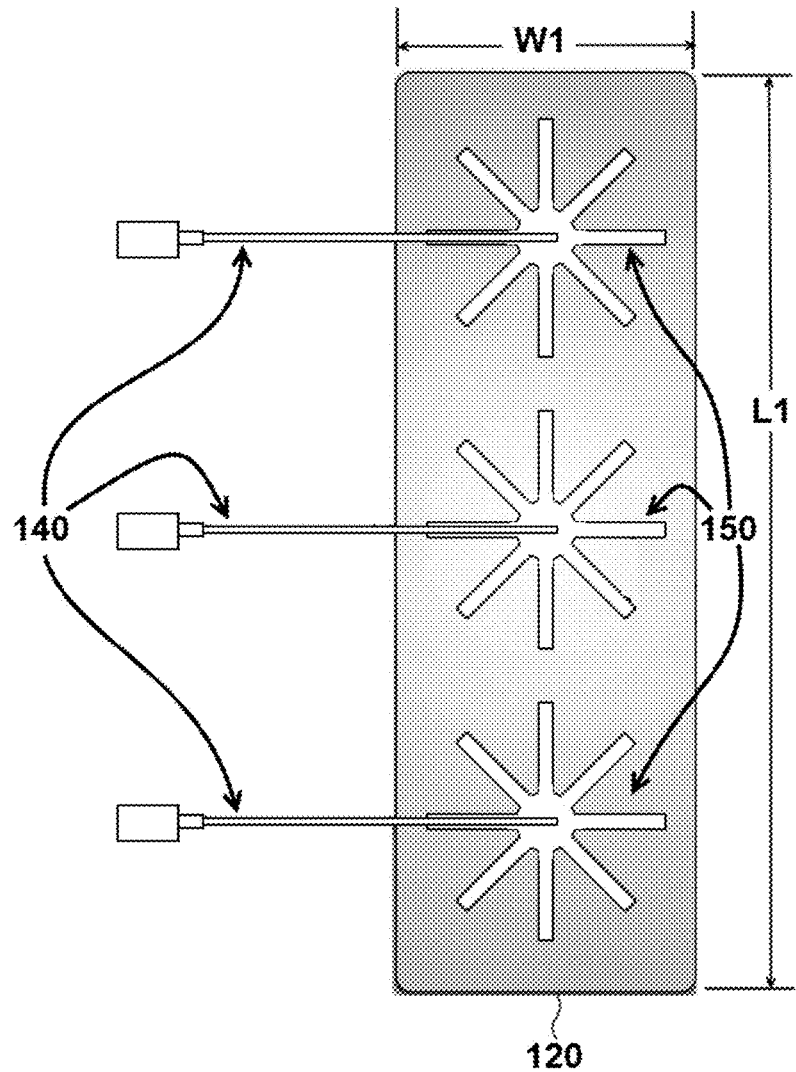
FIG. 6 is a top view of components compatible with the embodiment of FIG. 1.

Referring now to FIG. 6, another exemplary embodiment comprises a spacer material 120 with multiple conduits 140 in fluid communication with a plurality of distribution channels 150. In this exemplary embodiment, three separate conduits 140 are in fluid communication with three separate regions of distribution channels 150. Such a configuration can be particularly advantageous, for example, if spacer material 120 comprises length L1 that is greater than width W1 to cover a wound that is elongated in shape.

Figure 7:
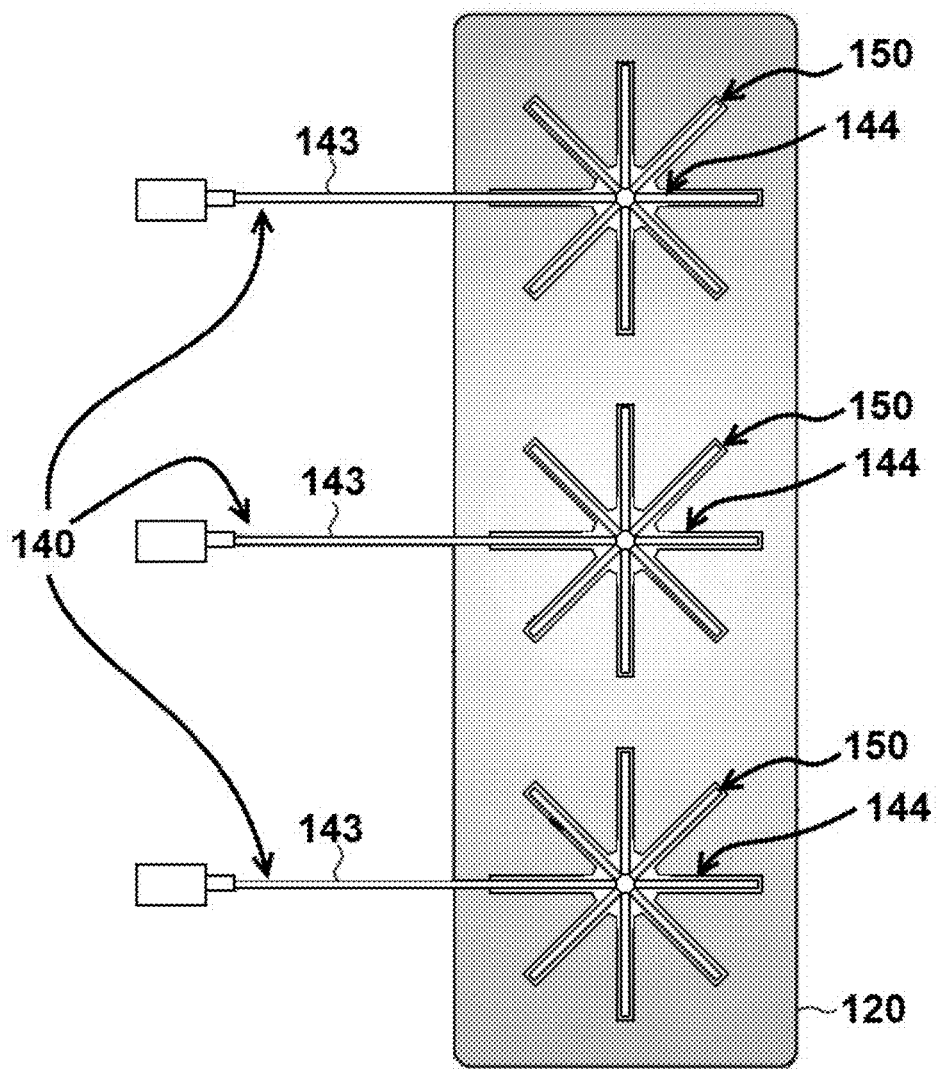
FIG. 7 is a top view of components compatible with the embodiment of FIG. 1.

Referring now to FIG. 7, another exemplary embodiment comprises a spacer material 120 with multiple conduits 140 in fluid communication with, and extending into, a plurality of distribution channels 150. In this exemplary embodiment, conduits 140 comprise three primary branches 143 that each extend to one of three separate regions of distribution channels 150. Conduits 140 also comprise secondary branches 144 that each extend into an individual distribution channel in the plurality of distribution channel 150. Such a configuration can be particularly advantageous, for example, if spacer may be subjected to compressive forces during use (if used with multi-layer compression wrap for venous ulcers, for example) that may compress spacer material 120 and collapse distribution channels 150. Without secondary branches 144, excessive compression of spacer material 120 and the collapse of distribution channels 150 could restrict flow of therapeutic fluid to a wound.

Figure 8:
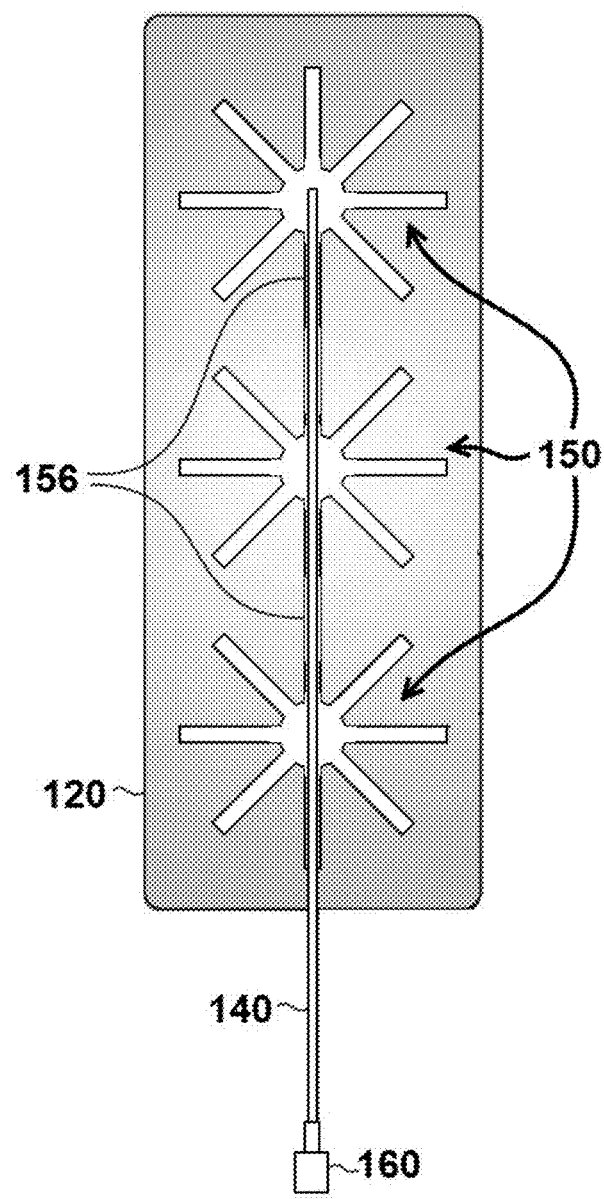
FIG. 8 is a top view of components compatible with the embodiment of FIG. 1.

Referring now to FIG. 8, another exemplary embodiment comprises a coupling mechanism 160 coupled to a conduit 140 that extends along a primary distribution channel 156 that is in fluid communication with multiple regions of branched distribution channels 150 in spacer material 120. Such a configuration can be particularly advantageous, for example, if spacer material comprises length L1 that is greater than width W1 and only a single conduit 140 is desired to access distribution channels 150. Similar to the embodiment shown in FIG. 5, conduit 140 may comprise a plurality of apertures (not shown for purposes of clarity) that increase in diameter as the distance between each aperture and coupling mechanism 160 increases.

Figure 9:
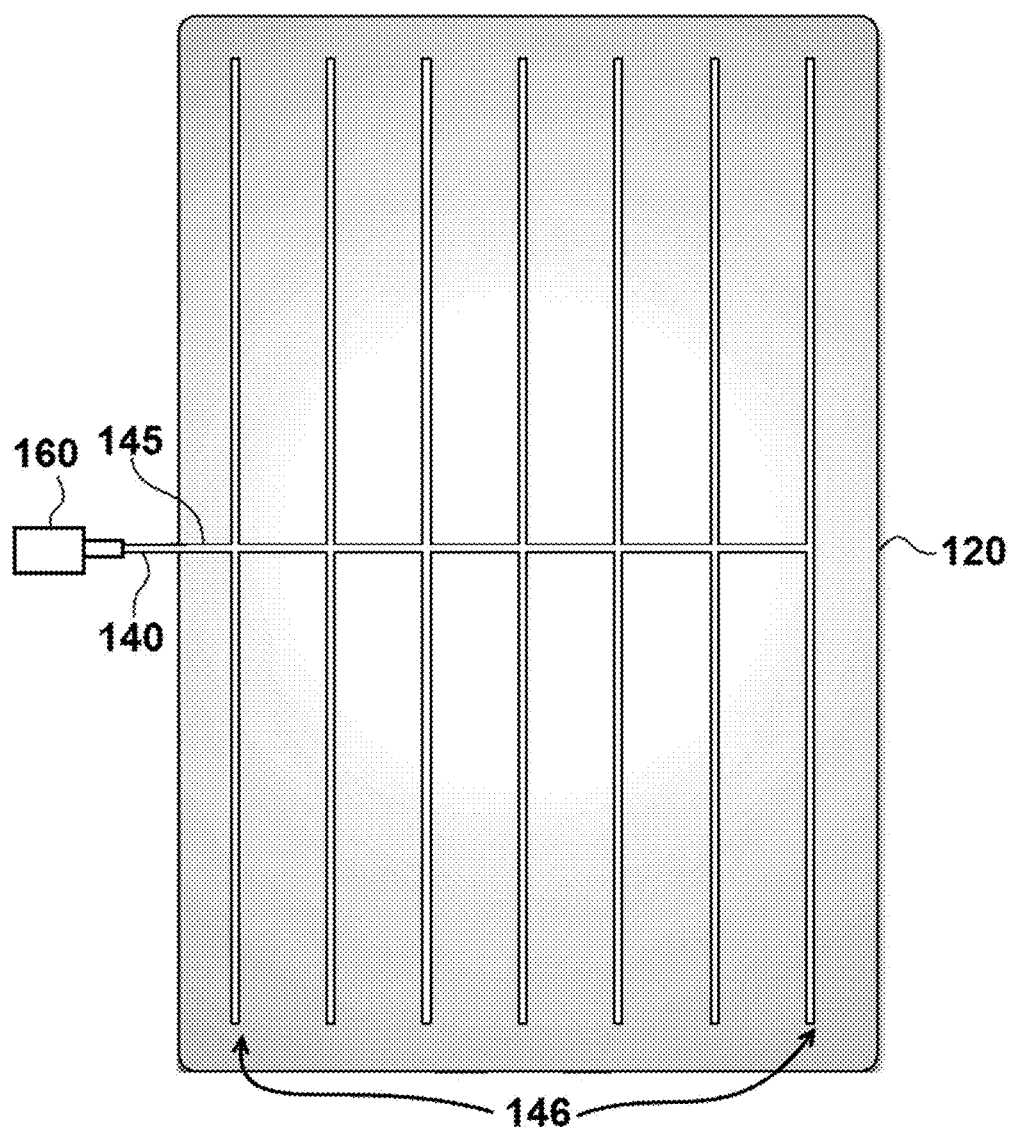
FIG. 9 is a top view of components compatible with the embodiment of FIG. 1.

Referring now to FIG. 9, another exemplary embodiment comprises a conduit 140 that comprises a primary branch 145 that extends across a central region of spacer material 120 and secondary branches 146 that extend away from primary branch 145 towards the outer perimeter of spacer material 120. Although not shown for purposes of clarity, secondary branches 146 (and optionally, primary branch 145) can comprise a plurality of apertures to provide for the delivery of oxygen or other therapeutic fluids to the surface of spacer material 120. In certain embodiments, the apertures may increase in diameter as the apertures progress away from primary branch 145 and/or coupling mechanism 160. In certain embodiments, the configuration of conduit 140 shown in FIG. 9 can be located within separate distribution channels (not shown) formed in spacer material 120. In the embodiment shown, the configuration of conduit shown in FIG. 9 can be located adjacent to the surface of spacer material 120 rather than within separate distribution channels formed in spacer material 120. In such embodiments, the secondary branches 146 serve as distribution channels.

Figure 10:
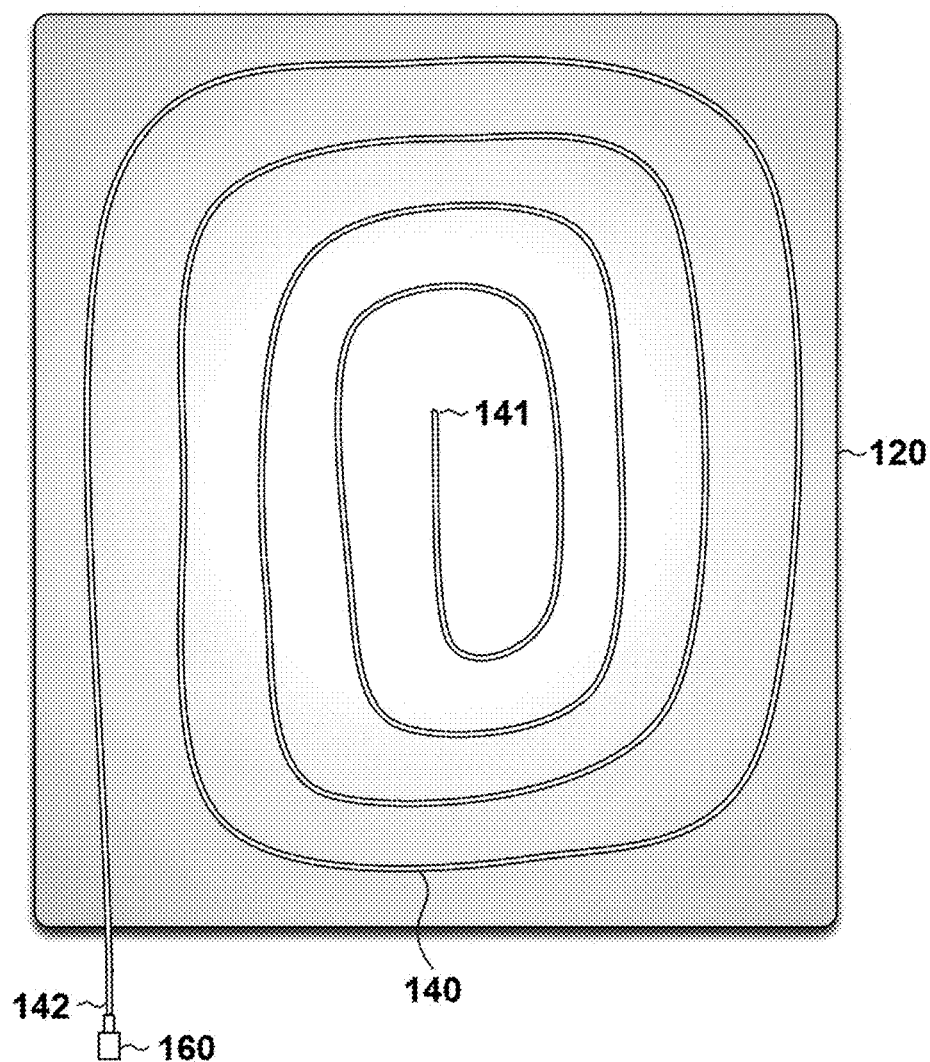
FIG. 10 is a top view of components compatible with the embodiment of FIG. 1.

Referring now to FIG. 10, another exemplary embodiment comprises a conduit 140 that comprises a generally spiral shape that extends from the perimeter of spacer material 120 toward the center of spacer material 120. Although not shown for purposes of clarity, conduit 140 can comprise a plurality of apertures to provide for the delivery of oxygen or other therapeutic fluids to the surface of spacer material 120. In certain embodiments, the apertures may increase in diameter as the apertures progress away from coupling mechanism 160 and and toward first end 141. In certain embodiments, the configuration of conduit 140 shown in FIG. 10 can be located within a distribution channel in spacer material 120. In other embodiments, the configuration of conduit shown in FIG. 10 may be located adjacent to the surface of spacer material 120 rather than within the distribution channel.

While various examples of apertures 170 and distribution channels 150 are illustrated in FIGS. 1-10, it is understood that other embodiments of the present disclosure may comprise different patterns or arrangements of the apertures and/or distribution channels. For example, distribution channels can be formed in concentric rings or polygons, a "snowflake" pattern, or other geometric shapes. Configurations of apertures 170 and distributions channels 150 can be used to enable oxygen therapy on a greater surface area of the wound site in a more uniform distribution. As such, any shape or pattern of distribution channels 150 may be provided depending on the wound. The distribution channels 150 in spacer material 120 may also be designed to allow oxygen to be delivered directly to small amounts of exudate from the wound.

In addition, certain embodiments may also comprise a distribution channel that runs along the length of a suture. Surgical wounds in obese patients are a particular type of acute wound that presents clinical problems rooted in inadequate oxygen distribution to tissues. Adipose tissue is inherently poorly vascularized and thus gets relatively less oxygen than other soft tissues. Additional embodiments may comprise a cannula that has apertures along an intra-wound portion of the cannula to deliver oxygen or other therapeutic fluids.

While a generally square dressing is illustrated herein, the shape and size of dressing 100 may be selected based on the wound site and area of the body it is being applied to.

In certain embodiments, dressing 100 may also have an identifier (e.g., located on coupling mechanism 160) that allows an attached device (e.g., an oxygen delivery system computer) to detect what the construction of the dressing is, sensors (e.g., pressure sensors, temperature sensors, etc.) that allow the monitoring of properties of the wound site so that oxygen flow rate, pressure, and/or other properties at the wound site may be adjusted based on output from such sensors.

Exemplary embodiments also provide for methods of treatment utilizing wound dressing 100. For example, wound dressing 100 can be placed so that first layer 130 is in contact with a wound. In certain methods, a therapeutic fluid (e.g. oxygen) can be delivered through conduit 140 to apertures 170 and/or the plurality of distribution channels 150. Certain methods of treatment may comprise measuring a first parameter and adjusting a second parameter related to the delivery of the therapeutic fluid through the conduit. In certain embodiments, the reading parameter may be a temperature, pressure, or pH reading, and the second parameter may be a therapeutic fluid flow rate or pressure.

Experimental Results

Figure 11:
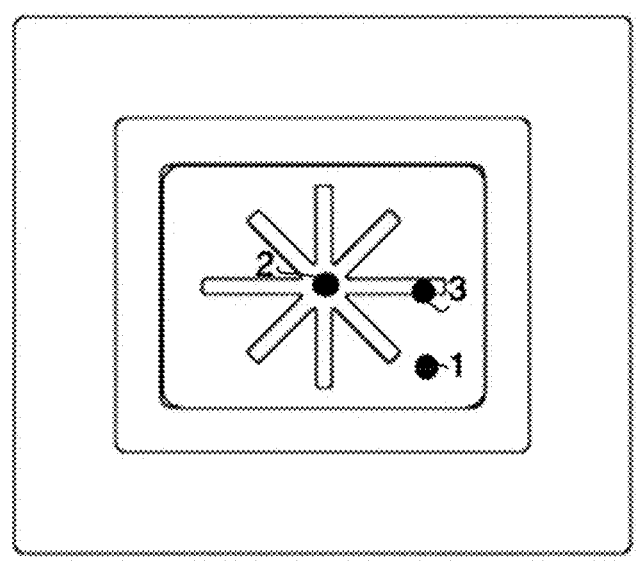
FIG. 11 is a schematic view of oxygen sensor locations used during testing of the embodiment of FIG. 3 and a reference dressing.

Experimental data was obtained to demonstrate the diffusion performance characteristics of the embodiments disclosed herein. Specifically, testing was performed using dressing 100 as shown and described in FIG. 3, hereinafter referred to as the "Oxygen Diffusion Dressing" (ODD). The oxygen concentration was measured in different locations throughout the ODD during testing. These measurements were compared to oxygen concentration measurements taken in a reference dressing that was similar to the ODD, but did not include spacer material 120. In addition, the reference dressing included a conduit with a single exit aperture located at the center of the dressing. In contrast, the ODD included conduit 140 with multiple apertures 170, which were also centered in the ODD during the testing. The locations of the different measurement points are shown in FIG. 11, and the results of the oxygen concentration measurements are shown in FIGS. 12-14.

As previously discussed in the description of the FIG. 3 the ODD (i.e., dressing 100) comprises an occlusive layer 110, a spacer material 120, a first layer 130 and a conduit 140. Spacer material 120 is located between occlusive layer 110 and first layer 130, and spacer material 120 comprises a plurality of distribution channels 150 in fluid communication with conduit 140. The ODD tested also included second absorbent layer 190 between occlusive layer 110 and spacer material 120. During testing, second layer 190 can function to keep distribution channels 150 in spacer material 120 open under a wider range of exudate levels.

During testing, both dressings were saturated with deionized water and placed under slight compression. Oxygen probes were used to measure the oxygen concentration at three locations in the space below the dressing (e.g., representative of a wound space) per FIG. 11. The oxygen probes were calibrated to read 100% saturation at room temperature with normal atmosphere (approximately 21% oxygen) saturating the solution prior to initiation of the test. Oxygen was introduced to each dressing at time 0 and monitored for 20 hours.

Figure 12:
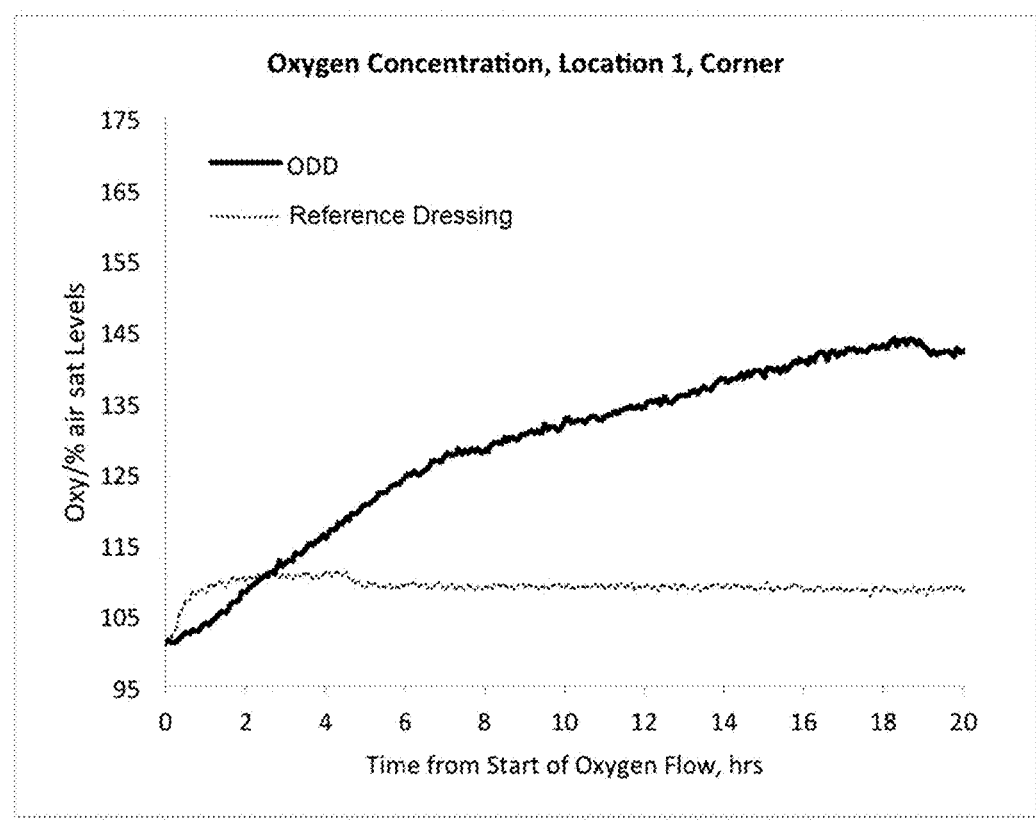
FIG. 12 is a graph of oxygen concentration measured during testing at a first location as shown in FIG. 11.
Figure 13:
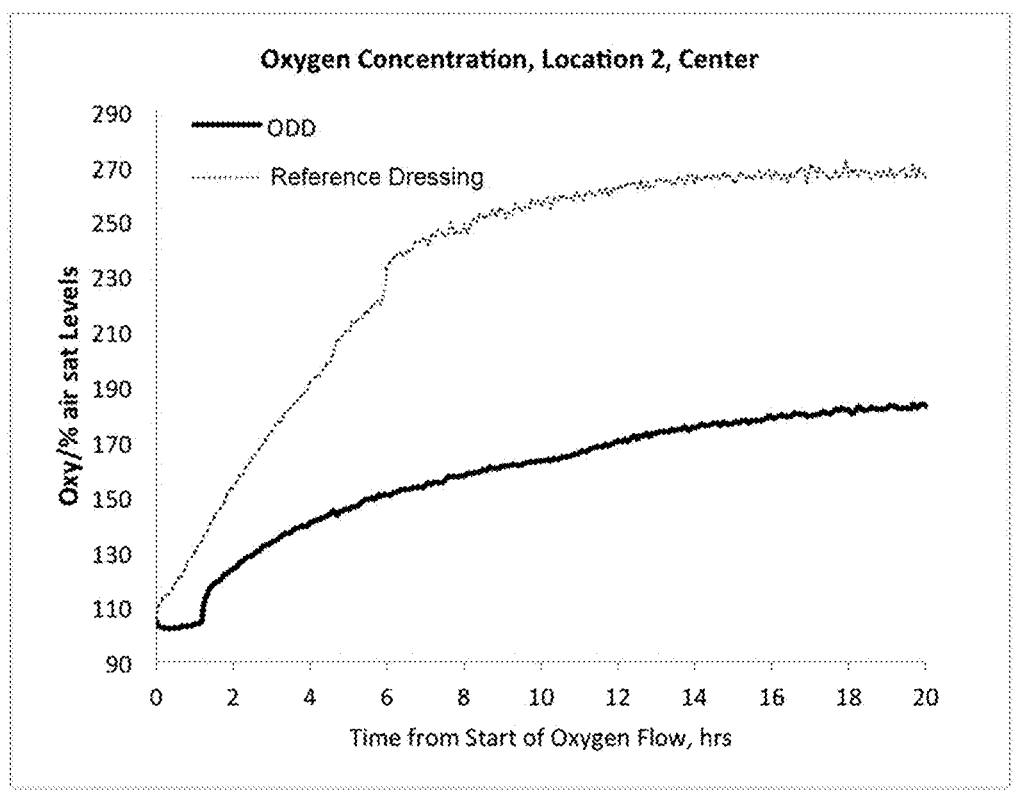
FIG. 13 is a graph of oxygen concentration measured during testing at a second location as shown in FIG. 11.
Figure 14:
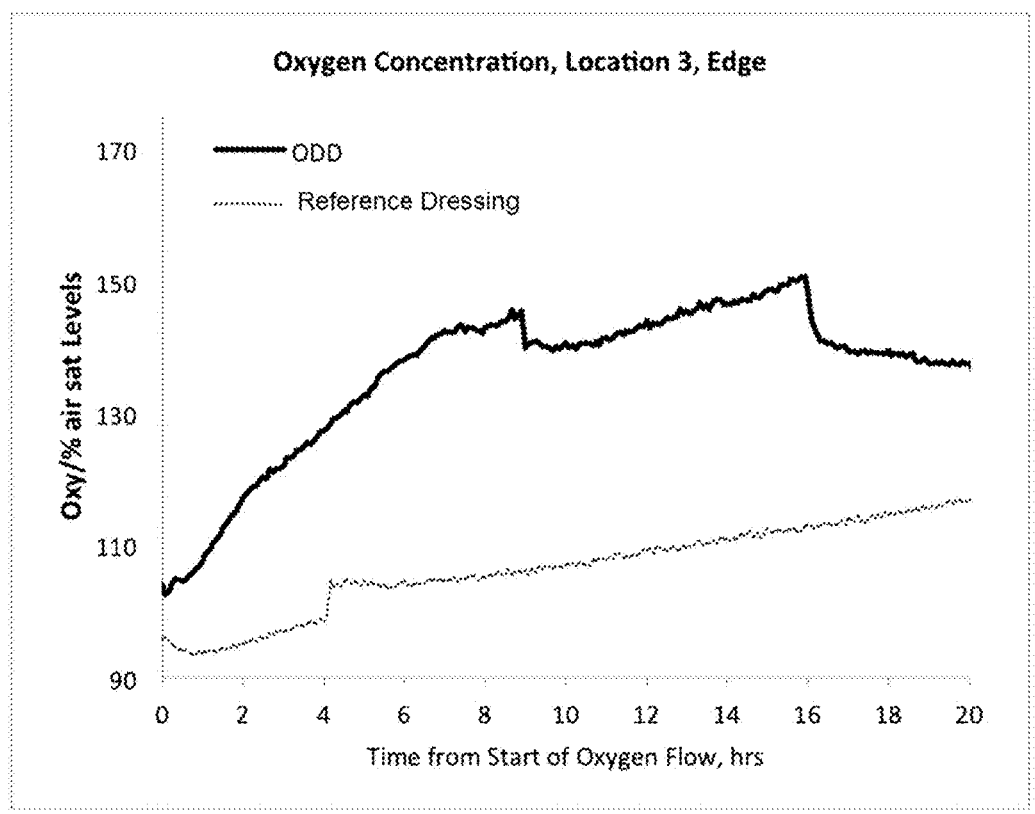
FIG. 14 is a graph of oxygen concentration measured during testing at a third location as shown in FIG. 11.

The resulting oxygen concentration curves for each location are shown in FIGS. 12-14. The oxygen point of delivery for both dressing types was centered around Location 2 as shown in FIG. 11. As can be seen from FIG. 13, the reference dressing has a faster rise and eventual maximum oxygen concentration than does the ODD at the center of the dressing where the oxygen is being delivered. However, the oxygen curves for both the corner and edge measurements, FIGS. 12 and 14, respectively, indicate that the ODD has both a faster rate of transfer (slope of curve) and maximum oxygen concentration than does the reference dressing at locations other than the point of distribution. All of these curves support the hypothesis that the decreased diffusion distance contributes to increasing the rate of delivery and maximum concentration of oxygen. The oxygen concentration for the reference dressing varies between 105 to 115% at the edge and corner to 260 to 270% oxygen (full saturation) in the center. The ODD has a much more even oxygen distribution over the space below the dressing, with 140 to 155% at both the edge and corner to 175 to 185% in the center. The distribution system offered by the ODD through the channeling of oxygen within the dressing to create a more even distribution above first layer 130 does indeed result in an overall higher concentration, a more even concentration, and a higher overall rate of concentration increase in the oxygen below first layer 130.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
U.S. Pat. No. 4,969,881
U.S. Pat. No. 6,458,109
U.S. Pat. No. 7,216,651
U.S. Pat. No. 7,263,814
U.S. Pat. No. 7,429,252
U.S. Pat. No. 7,790,945
U.S. Pat. No. 7,938,790
U.S. Pat. No. 8,084,663
U.S. Pat. No. 8,088,113
U.S. Pat. No. 8,235,955
U.S. Pat. No. 8,287,506
U.S. Pat. Pub. 2012/0046603
U.S. Pat. Pub. 2003/0212357
U.S. Pat. Pub. 2001/0041188
W.O. 2010/139926A1
Knighton, D. R., Silver, I. A., and Hunt, T. K. Regulation of wound-healing angiogenesis-effect of oxygen gradients and inspired oxygen concentration. Surgery 90:262-270, 1981.
Hunt, T. K. and Pai, M. P. The effect of varying ambient oxygen tensions on wound metabolism and collagen synthesis. Surg Gynecol Obstet 135:561-567, 1972.
Bosco, M. C., Delfino, S., Ferlito, F., Puppo, M., Gregorio, A., Gambini, C., Gattorno, M., Martini, A., and Varesio, L. The hypoxic synovial environment regulates expression of vascular endothelial growth factor and osteopontin in juvenile idiopathic arthritis. J Rheumatol 36:1318-1329, 2009.
Hohn, D. C., MacKay, R. D., Halliday, B., and Hunt, T. K. Effect of O2 tension on microbicidal function of leukocytes in wounds and in vitro. Surg Forum 27:18-20, 1976.

The invention claimed is:
1. A dressing for wound treatment comprising:
an occlusive layer;
a spacer material;
a plurality of distribution channels formed in the spacer material;
a first layer, wherein the spacer material is located between the occlusive layer and the first layer; and
a first conduit in fluid communication with the plurality of distribution channels, wherein:
the plurality of distribution channels extend from a central region of the spacer material toward a perimeter of the spacer material to evenly distribute a concentration of a therapeutic fluid from the first conduit to the first layer.

2. The dressing of claim 1 wherein the first conduit comprises a first end proximal to spacer material and a second end distal to the spacer material.

3. The dressing of claim 2 wherein the first conduit comprises a plurality of apertures.

4. The dressing of claim 3 wherein the plurality of apertures are arranged along an axial length of the first conduit.

5. The dressing of claim 4 wherein the plurality of apertures are arranged in order of increasing diameter toward the first end of the first conduit.

6. The dressing of claim 3 wherein the plurality of apertures are proximal to the first end of the first conduit.

7. The dressing of claim 3 wherein a first aperture is proximal to the first end and a second aperture is distal to the first end, and wherein a diameter of the first aperture is greater than or equal to a diameter of a second aperture.

8. The dressing of claim 2 wherein the conduit comprises a first aperture and a second aperture, and wherein:
a distance between the first aperture and the first end of the first conduit is less than a distance between the first end of the first conduit and the second aperture; and
a diameter of the first aperture is greater than or equal to a diameter of the second aperture.

9. The dressing of claim 8 further comprising a third aperture, wherein:
a distance between the third aperture and the first end of the first conduit is greater than the distance between the second aperture and the first end of the first conduit; and
the diameter of the second aperture is greater than or equal to the diameter of the third aperture.

10. The dressing of claim 2 wherein the first conduit comprises a first aperture, a second aperture, and a third aperture, wherein:
the first aperture is located a first distance from the first end of the first conduit;
the second aperture is located a second distance from the first end of the first conduit;
the third aperture is located a third distance from the first end of the first conduit;
the first distance is less than the second distance;
the second distance is less than the third distance;
the diameter of the first aperture is greater than or equal to the diameter of the second aperture; and
the diameter of the second aperture is greater than or equal to the diameter of the third aperture.

11. The dressing of claim 1 further comprising a source of fluid flow coupled to the first conduit.

12. The dressing of claim 11 wherein the source of fluid flow is configured to alter a fluid flow rate based on an output from a sensor.

13. The dressing of claim 12 wherein the sensor is configured to measure temperature.

14. The dressing of claim 12 wherein the sensor is configured to measure pH.

15. The dressing of claim 11 wherein the source of fluid flow is configured to provide a variable flow rate of a fluid.

16. The dressing of claim 1 wherein the occlusive layer comprises an adhesive.

17. The dressing of claim 16 wherein occlusive layer comprises a first surface proximal to the spacer material, a second surface distal to the spacer material, and a perimeter extending around the occlusive layer and wherein the adhesive extends around the perimeter of the first surface.

18. The dressing of claim 16 wherein the adhesive comprises a hydrocolloid.

19. The dressing of claim 1 further comprising a second layer, wherein the second layer is an absorbent layer located between the spacer material and the occlusive layer.

20. The dressing of claim 19 wherein the second absorbent layer comprises an alginate.

21. The dressing of claim 1 wherein the plurality of distribution channels comprise additional conduits in fluid communication with the first conduit, and wherein the additional conduits are adjacent to the spacer material.

22. The dressing of claim 1 wherein the first layer comprises a first surface proximal to the spacer material and a second surface distal to the spacer material, and wherein the second surface is a non-adherent surface.

23. The dressing of claim 1 further comprising a non-adherent layer, wherein the first layer is located between the non-adherent layer and the spacer material.

24. The dressing of claim 1 wherein the first layer is an absorbent layer.

25. The dressing of claim 1 wherein the first layer is an absorbent layer with a non-adherent surface distal to the spacer material.

26. The dressing of claim 1 wherein the first layer is a contact layer.

27. The dressing of claim 1 wherein the first layer is configured as a silicone non-adherent layer.

28. The dressing of claim 1, further comprising a plurality of conduits in fluid communication with the plurality of distribution channels.

29. The dressing of claim 1 wherein the first conduit is configured to withstand a compressive pressure of 200 mm Hg without occluding a fluid flow through the conduit.

30. The dressing of claim 1 further comprising an oxygen delivery device coupled to the first conduit.

31. The dressing of claim 1 wherein the plurality of distribution channels comprises eight channels that extend from a central region of the spacer material toward a perimeter of the spacer material.

32. The dressing of claim 1 wherein the plurality of distribution channels are configured in a spiral pattern.

33. The dressing of claim 1 wherein:
the spacer material has a length and a width;
each of the distribution channels has a length;
the combined length of the distribution channels is greater than the length of the spacer material; and
the combined length of the distribution channels is greater than the width of the spacer material.

34. A method of providing a therapeutic fluid to a wound, the method comprising:
providing a dressing for wound treatment comprising:
an occlusive layer;
a spacer material;
a plurality of distribution channels;
a first layer, wherein the spacer material is located between the occlusive layer and the first layer; and
a first conduit in fluid communication with the plurality of distribution channels;
placing the first layer in contact with the wound; and
delivering a therapeutic fluid through the first conduit to the plurality of distribution channels, wherein:
the plurality of distribution channels are formed in the spacer material and extend from a central region of the spacer material toward a perimeter of the spacer material; and
the plurality of distribution channels evenly distribute a concentration of the therapeutic fluid from the first conduit to the first layer.

35. The method of claim 34 further comprising:
measuring a first parameter; and
adjusting a second parameter related to the delivery of the therapeutic fluid through the first conduit.

36. A method of providing a therapeutic fluid to a wound, the method comprising:
providing a dressing for wound treatment comprising:
an occlusive layer;
a spacer material;
a plurality of distribution channels;
a first layer, wherein the spacer material is located between the occlusive layer and the first layer; and
a conduit;
placing the first layer in contact with the wound; and
delivering a therapeutic fluid through the conduit to the spacer material, wherein the conduit comprises a plurality of apertures, and wherein:
the plurality of distribution channels are formed in the spacer material and extend from a central region of the spacer material toward a perimeter of the spacer material; and
the plurality of distribution channels evenly distribute a concentration of the therapeutic fluid from the first conduit to the first layer.

37. The method of claim 36 further comprising:
measuring a first parameter; and
adjusting a second parameter related to the delivery of the therapeutic fluid through the conduit.

38. A dressing for wound treatment comprising:
an occlusive layer;
a spacer material;
a plurality of distribution channels;
a first layer, wherein the spacer material is located between the occlusive layer and the first layer; and
a first conduit in fluid communication with the spacer material, wherein the conduit comprises a plurality of apertures, wherein:
the plurality of distribution channels are formed in the spacer material and extend from a central region of the spacer material toward a perimeter of the spacer material to evenly distribute a concentration of a therapeutic fluid from the first conduit to the first layer.

* * * * *